United States Patent
Froelich et al.

(12) 
(10) Patent No.: US 6,458,826 B2
(45) Date of Patent: Oct. 1, 2002

(54) COMPOSITION FOR REPELLING AND DETERRING PESTS

(75) Inventors: Olivier Froelich, Kembs (FR); Jacques Bouvier, Neuchatel (CH); Catherine Christinaz, Gletterens (CH); Nicola Di Criscio, Basel (CH)

(73) Assignee: Navartis Animal Health US, Inc., Greensboro, NC (US)

( * ) Notice: Subject to any disclaimer, the term of this patent is extended or adjusted under 35 U.S.C. 154(b) by 0 days.

(21) Appl. No.: 09/738,106

(22) Filed: Dec. 15, 2000

Related U.S. Application Data

(63) Continuation of application No. PCT/EP99/04174, filed on Jun. 16, 1999.

(30) Foreign Application Priority Data

Jun. 18, 1998 (CH) .............................................. 1319/98

(51) Int. Cl.⁷ .............................................. A01N 43/36
(52) U.S. Cl. ........................ 514/428; 548/570; 424/405
(58) Field of Search ......................... 514/428; 548/570; 424/405

(56) References Cited

U.S. PATENT DOCUMENTS

| | | | | |
|---|---|---|---|---|
| 4,248,884 A | * | 2/1981 | Legrand et al. | 424/274 |
| 4,299,840 A | | 11/1981 | Skinner et al. | 424/274 |
| 4,625,038 A | * | 11/1986 | Thottahil | 548/570 |
| 4,746,199 A | * | 5/1988 | Nicoud et al. | 350/354 |
| 4,873,252 A | | 10/1989 | Kruger et al. | 514/315 |
| 4,880,827 A | * | 11/1989 | Tamoto et al. | 514/423 |
| 4,950,767 A | * | 8/1990 | Kraatz | 548/570 |
| 5,650,521 A | * | 7/1997 | Jackson | 548/556 |

FOREIGN PATENT DOCUMENTS

| | | |
|---|---|---|
| EP | 0 238 319 | 9/1987 |
| EP | 0 281 908 | 9/1988 |

\* cited by examiner

*Primary Examiner*—Fiona T. Powers
(74) *Attorney, Agent, or Firm*—Michael U. Lee

(57) ABSTRACT

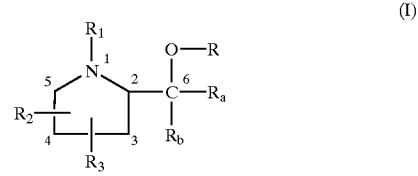

The invention describes essentially a non-therapeutical process for deterring vermin, which is based on the usage of the largely known compounds of formula (I), as defined herein before. Furthermore, it describes the corresponding vermin-deterring compositions which contain these substances as the active ingredient, compounds of the formula (I) for the preparation of vermin-deterring compositions, and the use of compounds of formula (I) in the defence against vermin. Thus, the invention describes how and in which form the compounds of the formula (I) or their acid addition salts are used to deter vermin from materials, places or warm-blooded animals.

15 Claims, No Drawings

COMPOSITION FOR REPELLING AND DETERRING PESTS

This is a continuation of International Application No. PCT/EP 99/04174, filed Jun. 16, 1999, the contents of which are incorporated herein by reference.

The present invention relates essentially to a non-therapeutical process for deterring vermin, which is based on the usage of the largely known compounds of formula (I) shown below. Furthermore, it relates to corresponding vermin-repelling compositions which contain these substances as the active ingredient, to compounds of formula (I) for the preparation of vermin-deterring compositions, and to the use of compounds of formula (I) in the defence against vermin.

It has surprisingly been found that the compounds of formula (I) below

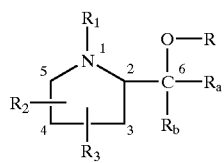

(I)

or their acid addition salts, wherein

R is hydrogen, $C_1$–$C_{20}$-alkyl or —C(O)—$R_8$, whereby $R_8$ is $C_1$–$C_{20}$-alkyl, $C_1$–$C_{20}$-alkoxy, unsubstituted phenyl or phenyl which is substituted once or many times by $C_1$–$C_3$-alkyl, $C_1$–$C_3$-haloalkyl, $C_1$–$C_3$-haloalkoxy, halogen, cyano, hydroxyl, alkoxy, amino or nitro;

$R_1$ is hydrogen, $C_1$–$C_{20}$-alkyl, —C(O)—$R_3$, —C(S)—$R_4$, C(O)—O—$R_5$, —C(O)—NH—$R_6$ or —C(S)—NH—$R_7$; whereby $R_3$, $R_4$, $R_5$, $R_6$ and $R_7$, independently of one another, signify $C_1$–$C_{10}$-alkyl, acetoxy, $C_1$–$C_{10}$-haloalkyl, $C_1$–$C_{10}$-alkoxy or $C_1$–$C_{10}$-haloalkoxy, or independently of one another, denote unsubstituted phenyl or phenyl which is substituted once or many times by $C_1$–$C_3$-alkyl, $C_1$–$C_3$-haloalkyl, $C_1$–$C_3$-haloalkoxy, halogen, cyano, hydroxyl, $C_1$–$C_3$-alkoxy, amino, CHO or nitro;

$R_2$ and $R_3$, independently of one another, are hydrogen, $C_1$–$C_3$-alkyl, $C_1$–$C_3$-haloalkyl, $C_1$–$C_3$-haloalkoxy, halogen, cyano, hydroxyl, amino, aryl or nitro; p1 $R_a$ denotes hydrogen, unsubstituted $C_1$–$C_{20}$-alkyl or $C_1$–$C_{20}$-alkyl which is substituted once or many times by halogen, cyano, hydroxyl, alkoxy, nitro, phenyl, biphenyl, benzyloxy or phenoxyphenyl, whereby each phenyl, biphenyl, benzyloxy or phenoxyphenyl in turn is unsubstituted or substituted once or many times by $C_1$–$C_3$-alkyl, $C_1$–$C_3$-haloalkyl, $C_1$–$C_3$-haloalkoxy, $C_1$–$C_3$-alkoxy, halogen, cyano, hydroxyl, amino or nitro; or it denotes $C_3$–$C_8$ -cycloalkyl, phenyl, biphenyl, phenoxyphenyl or heterocyclyl, whereby each of these cyclic radicals is unsubstituted or substituted once or many times by $C_1$–$C_3$-alkyl, $C_2$–$C_6$-alkenyl, $C_1$–$C_3$-haloalkyl, $C_1$–$C_3$-haloalkoxy, $C_1$–$C_3$-alkoxy, halogen, cyano, hydroxyl, amino, ($C_1$–$C_3$alkyl)$_2$N, acetyl or nitro; or it denotes $C_1$–$C_6$-alkylene-aryl , whereby the aryl radical is unsubstituted or substituted once or many times by $C_1$–$C_3$-alkyl, $C_1$–$C_3$-haloalkyl, $C_1$–$C_3$-haloalkoxy, halogen, cyano, hydroxyl or nitro; or it denotes $C_1$–$C_{20}$-alkyl which, depending on the number of carbon atoms, is interrupted by oxygen at one or several positions; and $R_b$ signifies hydrogen, $C_1$–$C_{20}$-alkyl, heterocyclyl or aryl, whereby each of the cyclic radicals is unsubstituted or substituted once or many times by $C_1$–$C_3$-alkyl, $C_1$–$C_3$-haloalkyl, $C_1$–$C_3$-haloalkoxy, $C_2$–$C_6$-alkenyl, halogen, cyano, hydroxyl, $C_1$–$C_3$-alkoxy, amino, ($C_1$–$C_3$-alkyl)$_2$N, or nitro;

are eminently suitable for deterring vermin. Through the usage according to the invention of the above compounds, the most varied vermin of humans, animals, objects or certain places can be deterred, whereby numerous compounds within the scope of formula (I) are notable for their particularly long duration of efficacy.

Compounds of formula (I) having at least one basic centre may form e.g. acid addition salts. These are formed for example with strong inorganic acids, such as mineral acids, e.g. perchloric acid, sulphuric acid, nitric acid, nitrous acid, a phosphoric acid or a hydrohalic acid, with strong organic carboxylic acids, typically $C_1$–$C_4$alkanecarboxylic acids substituted where appropriate for example by halogen, e.g. acetic acid, such as dicarboxylic acids that are unsaturated where appropriate, e.g. oxalic, malonic, succinic, maleic, fumaric or phthalic acid, typically hydroxycarboxylic acids, e.g. ascorbic, lactic, malic, tartaric or citric acid, or benzoic acid, or with organic sulphonic acids, typically $C_1$–$C_4$alkanesulphonic or arylsulphonic acids substituted where appropriate for example by halogen, e.g. methanesulphonic or p-toluenesulphonic acid. Of the salts, particular preference is given to those formed with strong acids, especially with mineral acids, in particular with the hydrohalic acids HCl and HBr.

All multiple substitutions are to be interpreted such that identical or different substituents may occur simultaneously.

The alkyl groups present in the definitions of the substituents may be straight-chained or branched, depending on the number of carbon atoms, and they may be for example methyl, ethyl, propyl, butyl, pentyl, hexyl, heptyl, octyl, nonyl, decyl, undecyl, dodecyl, tetradecyl, hexadecyl, octadecyl or eicosyl, as well as the branched isomers thereof, for example isopropyl, isobutyl, sec.-butyl, tert.-butyl, isopentyl, neopentyl or isohexyl. Alkoxy, haloalkyl and haloalkoxy radicals are derived from the said alkyl groups.

Halo denotes halogen and normally signifies fluorine, chlorine, bromine or iodine, preferably fluorine or chlorine, especially chlorine, whereby the corresponding substituent may contain one or more identical or different halogen atoms.

Halogen-substituted carbon-containing groups, such as haloalkyl or haloalkoxy, may be partially halogenated or perhalogenated, whereby in the case of multiple halogenation, the halogen substituents may be identical or different. Examples of haloalkyl—as a group per se and as structural element of other groups and compounds such as haloalkoxy—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_{CHClF}$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; and butyl or one of its isomers, mono- to nonasubstituted by fluorine, chlorine and/or bromine, such as $CF(CF_3)CHFCF_3$ or $CH_2(CF_2)_2CF_3$.

Alkenyl—as a group per se and as structural element of other groups and compounds such as alkeneoxy, halogenalkenyl or halogenalkeneoxy—is, in each case with due consideration of the specific number of carbon atoms in the group or compound in question, either straight-chained, for example vinyl, 1-methylvinyl, allyl, 1-butenyl or 2-hexenyl, or branched, for example isopropenyl.

Appropriate cycloalkyl substituents contain 3 to 8 carbon atoms and are, for example, cyclopropyl, cyclobutyl, cyclopentyl, cyclohexyl, cycloheptyl or cyclooctyl. Corresponding cycloalkenyl substituents may be mono- or also repeatedly unsaturated, for example cyclopentadienyl or cyclooctatetraenyl. Cyclopentyl and cyclohexyl are preferred.

In the context of the present invention, aryl is understood to be phenyl or naphthyl, especially phenyl. These aryl groups are either unsubstituted or are substituted once or many times by $C_1$–$C_3$-alkyl, $C_1$–$C_3$-haloalkyl, $C_1$–$C_3$-alkoxy, $C_1$–$C_3$-haloalkoxy, halogen, cyano, hydroxyl, amino or nitro, whereby each multiple substitution is not limited to identical substituents; instead, mixed substituents may appear.

In the context of the present invention, heterocyclyl is understood to mean aliphatic or aromatic and additionally also benzo-condensed cyclic radicals, which contain at least one oxygen, sulphur or nitrogen atom. Five- and six-membered heterocycles are preferred. Heterocyclyl typically includes substituents such as dioxolanyl, pyrrolidinyl, piperidinyl, morpholinyl, pyridyl, pyrryl, furyl, thienyl, imidazolyl, tetrahydrofuryl, tetrahydropyrryl, tetrahydropyranyl, dihydrofuryl, dihydropyranyl, benzofuryl, benzothienyl, isoxazolyl, oxazolyl, thiazolyl, oxazolinyl, oxazolidinyl, indolyl, imidazolinyl, imidazolidinyl and dioxanyl. Preference is given especially to those which are unsubstituted or have one or two halogen atoms, halogen in this case denoting fluorine, chlorine or bromine, but especially chlorine. Of these heterocyclyl radicals, pyrrolidinyl, piperidinyl, pyridyl, pyrryl, furyl, thienyl, tetrahydrofuryl, benzofuryl and benzothienyl are especially notable.

A preferred sub-group in the context of formula (I) is formed by compounds wherein R is hydrogen or $C_1$–$C_6$alkyl;

$R_1$ is hydrogen, $C_1$–$C_6$-alkyl, —C(O)—$R_3$ or —C(S)—$R_4$; whereby $R_3$ and $R_4$ independently of one another, are $C_1$–$C_3$-alkyl, acetoxy, $C_1$–$C_3$-haloalkyl, or independently of one another, are unsubstituted phenyl or phenyl which is substituted once or many times by $C_1$–$C_3$-alkyl, $C_1$–$C_3$-haloalkyl or halogen;

$R_2$ and $R_3$ independently of one another, are hydrogen or $C_1$–$C_3$-alkyl;

$R_a$ is hydrogen, $C_5$–$C_{20}$-alkyl, $C_3$–$C_8$-cycloalkyl or phenyl, whereby each of the cyclic radicals is unsubstituted or is substituted once or many times by $C_1$–$C_3$-alkyl, $C_1$–$C_3$-haloalkyl, $C_1$–$C_3$-alkoxy, halogen, amino, $(C_1$–$C_3$-alkyl$)_2$N, or acetyl; and $R_b$ is hydrogen, unsubstituted phenyl or phenyl which is substituted once or many times by $C_1$–$C_3$-alkyl, $C_1$–$C_3$-haloalkyl, $C_1$–$C_3$-alkoxy, halogen, amino or $(C_1$–$C_3$-alkyl$)_2$N; including the acid addition salts thereof.

In the context of formula (I), the compounds which are especially preferred are those wherein R is hydrogen and the remaining substituents are defined as under formula (I), as well as the acid addition salts thereof. A further sub-group, which is preferred because of its marked activity, is formed by compounds of formula I, wherein $R_1$ is —C(O)—$R_3$, whereby $R_3$ represents unsubstituted phenyl or phenyl which is substituted once or many times by $C_1$–$C_3$-alkyl, especially by methyl, ethyl or isopropyl, and the remaining substituents are defined as under formula (I), as well as the acid addition salts thereof. Also of interest are the compounds of formula (I), wherein $R_2$ and $R_3$ independently of one another, are hydrogen or methyl, and the remaining substituents are defined as under formula (I), as well as the acid addition salts thereof. Of the above-mentioned compounds of formula (I), particular preference is given to those in which $R_a$ is $C_5$–$C_{20}$-alkyl, unsubstituted phenyl or phenyl which is substituted once or many times by $C_1$–$C_3$-alkyl, methoxy or chlorine; including the acid addition salts thereof, and in particular representatives in which $R_a$ is a straight-chained $C_7$–$C_{20}$-alkyl; including the acid addition salts thereof. The free active ingredients are clearly preferred over the acid addition salts.

Each representative of the group of individual substances listed below is especially preferred owing to its marked activity, those marked with the asterix being new and representing a constituent of the present invention:2-[n-(1-hydroxyhexyl)]pyrrolidine*, 2-[n-(1-hydroxyheptyl)]pyrrolidine*, 2-[n-(1-hydroxyheptyl)]-5-(tert.-butyl)pyrrolidine, 2-[n-(1-hydroxyheptyl)]-5-(n-butyl)pyrrolidine, 2-[n-(1-hydroxyoctyl)]pyrrolidine*, [n-(1-hydroxyoctyl)]-5-(n-propyl)-pyrrolidine, 2-[n-(1-hydroxynonyl)]pyrrolidine*, 2-[n-(1-hydroxydecyl)]pyrrolidine*, 2-[n-(1-hydroxyundecyl)]pyrrolidine*, 2-[n-(1-hydroxydodecyl)]pyrrolidine*, 2-[n-(1-hydroxytridecyl)]pyrrolidine*, 2-[n-(1-hydroxytetradecyl)]pyrrolidine*, 2-[n-(1-hydroxypentadecyl)]pyrrolidine*, 2-[n-(1-hydroxyhexadecyl)]pyrrolidine*, 2-[n-(1-hydroxyheptadecyl)]-pyrrolidine*, 2-[n-(1-hydroxyoctadecyl)]pyrrolidine*, 2-[n-(1-hydroxynonadecyl)]pyrrolidine*, 2-[n-(1-hydroxyeicosyl)]pyrrolidine*, 2-[n-(1-hydroxyeneicosyl)]pyrrolidine*, 2-[(1-phenyl)(1-hydroxy)methyl]pyrrolidine, 2-[(1-[4-chorophenyl])(1-hydroxy)methyl]pyrrolidine, 2-[(1-[2,4-dimethylphenyl])(1-hydroxy)methyl]-5,5-dimethyl-pyrrolidine or 2-[(1-[3-chlorophenyl])(1-hydroxy)methyl]-5,5-dimethyl-pyrrolidine.

EP-0,281,908 discloses the use of certain α,ω-aminoalcohol derivatives, e.g. some piperidines as insect and tick repellents. U.S. Pat. No. 4,299,840 discloses a process for repelling ticks and other biting insects comprising the topical administration of certain pyrrolidone derivatives to animals or humans. EP-0,238,319 discloses a group pyrrolidine derivatives as inhibitors for proline-specific endopeptidase but does not report on any repellent activity.

In the context of the present invention, vermin are understood to be in particular insects, mites and ticks. These include insects of the order: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera. However, the vermin which may be mentioned in particular are those which trouble humans or animals and carry pathogens, for example flies such as *Musca domestica, Musca vetustissima, Musca autumnalis, Fannia canicularis, Sarcophaga camaria, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Stomoxys calcitrans, Haematobia irritans* and midges (Nematocera), such as Culicidae, Simulmiidae, Psychodidae, but also blood-sucking vermin, for example fleas, such as *Ctenocephalides felis* and *Ctenocephalides canis* (cat and dog fleas), *Xenopsylla cheopis, Pulex irritans, Dermatophilus penetrans, lice,* such as *Damalina ovis, Pediculus humanis,* biting flies and horseflies (Tabanidae), Haematopota spp. such as *Haematopota pluvialis,* Tabanidea spp. such as *Tabanus nigrovittatus,* Chrysopsinae spp. such as *Chrysops caecutiens,* tsetse flies, such as species of Glossinia, biting insects, particularly cockroaches, such as *Blatella germanica, Blatta orientalis,*

*Periplaneta americana,* mites, such as *Dermanyssus gallinae, Sarcoptes scabiei, Psoroptes ovis* and Psorergates spp. and last but not least ticks. The latter belong to the order Acarina. Known representatives of ticks are, for example, Boophilus, Amblyomma, Anocentor, Dermacentor, Haemaphysalis, Hyalomma, Ixodes, Rhipicentor, Margaropus, Rhipicephalus, Argas, Otobius and Ornithodoros and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

Ticks may be divided into hard and soft ticks, and are characterised by infesting one, two or three host animals. They attach themselves to a passing host animal and suck the blood or body fluids. Fully engorged female ticks drop from the host animal and lay large amounts of eggs (2000 to 3000) in a suitable crack in the floor or in any other protected site where the larvae hatch. These in turn seek a host animal, in order to suck blood from it. Larvae of ticks which only infest one host animal moult twice and thus become nymphs and finally adult ticks without leaving the host they have selected. Larvae of ticks which infest two or three host animals leave the animal after feeding on the blood, moult in the local environment and seek a second or third host as nymphs or as adult ticks, in order to suck its blood.

Ticks are responsible world-wide for the transmission and spread of many human and animal diseases. Because of their economic influence, the most important ticks are Boophilus, Rhipicephalus, Ixodes, Hyalomma, Amblyomma and Dermacentor. They are carriers of bacterial, viral, rickettsial and protozoal diseases and cause tick-paralysis and tick-toxicosis. Even a single tick can cause paralysis whereby its saliva penetrates into the host animal during ingestion. Diseases caused by ticks are usually transmitted by ticks, which infest several host animals. Such diseases, for example babesiosis, anaplasmosis, theileriasis and heart water disease, are responsible for the death or impairment of a large number of domestic and farm animals in the entire world. In many countries of temperate climate, Ixodide ticks transmit the agent of the chronically harmful Lyme's disease from wild animals to humans. Apart from the transmission of disease, the ticks are responsible for great economic losses in livestock production. Losses are not confined to the death of the host animals, but also include damage to the pelts, loss of growth, a reduction in milk production and reduced value of the meat. Although the harmful effects of a tick infestation on animals have been known for years, and enormous progress has been made using tick-control programmes, until now no completely satisfactory methods of controlling or eliminating these parasites have been found, and in addition, ticks have often developed resistance to chemical active ingredients.

The infestation of fleas on domestic animals and pets likewise still represents for the owner a problem which has not been satisfactorily resolved or can only be resolved at considerable expense. As with ticks, fleas are not only troublesome, but are carriers of disease, and transmit various fungal diseases from host animal to host animal and to the animal keeper, particularly in moist, warm climatic areas, for example in the Mediterranean, in the southern part of USA, etc. Those at risk in particular are people with a weakened immune system or children whose immune system has not yet fully developed. Owing to their complex life cycle, none of the known methods for the control of fleas is completely satisfactory, especially as most known methods are basically directed towards the control of adult fleas in the pelt, and leave completely untouched the different juvenile stages of the fleas, which exist not only in the pelt of the animal, but also on the floor, in carpets, in the bedding of the animal, on chairs, in the garden and all other places with which the infested animal comes into contact. Flea treatment is usually expensive and has to be continued over long periods of time. Success usually depends on treating not only the infested animal, e.g. the dog or cat, but at the same time all the locations which the infested animal frequents.

Such a complicated procedure is unnecessary with the present compounds of formula (I( ), since a particular advantage of the compounds of formula (I) under discussion is that they are extremely effective and at the same time of very low toxicity both for the target parasites and for the warm-blooded animals. This is because their activity is based not on the death of the target parasite, but on the parrying defence thereof, before it attacks, sting, bites or in any other way harms the host organism. The presence of the compounds of formula (I) being discussed here appears to disturb the parasites in such a way that they suddenly leave the treated environment without biting or stinging, or even do not infest a treated host animal at all. What is striking is that the effect sets in when the parasite comes into contact with the active ingredient for a short time. After contact for a short time, the parasite avoids any further contact with the active ingredient. An additional advantage lies in the long-term action, e.g. compared with DEET (N,N-diethyl-m-toluamide), which although very effective, volatilizes rather rapidly and therefore has to be reapplied already after ca. 2 hours, and is thus not appropriate for the long-term treatment of animals. Usage of the present active ingredients is also pleasant because they are almost odourless.

Although the present active ingredients can of course be mixed with other substances having the same sphere of activity or with parasiticides or with other activity-improving substances to achieve further improved or longer-lasting action, and then applied, in contrast to many compounds of the prior art, this is totally unnecessary, as they already combine all the advantageous properties.

If the parasite is not only to be kept at bay, but also killed, of course this can be achieved by adding appropriate insecticides and/or acaricides. In practice, however, this is unnecessary in most cases.

The present active ingredients are preferably used in diluted form. Normally, they are brought to the final application form by using appropriate formulation excipients, and they then contain between 0.1 and 95% by weight, preferably 0.5 to 90% by weight of the active ingredient.

Since the active ingredients are in many instances applied to warm-blooded animals and of course come into contact with the skin, suitable formulation excipients are the excipients and administration forms that are known in cosmetics. They may be administered in the form of solutions, emulsions, ointments, creams, pastes, powders, sprays, etc.

For administration to farm animals or pets, such as cows, horses, asses, camels, dogs, cats, poultry, sheep, goats, etc., the so-called 'pour-on' or 'spot-on' formulations are especially suitable; these liquid or semi-liquid formulations have the advantage that they only have to be applied to a small area of the pelt or plumage, and, thanks to the proportion of spreading oils or other spreading additives, they disperse by themselves over the whole pelt or plumage, without having to do anything else, and become active over the whole area.

Of course, inanimate materials, for example clothing or dog and cat baskets, stables, carpets, curtains, living quarters, conservatories, etc. may be treated with said formulations and thus protected from parasite infestation.

To control cockroaches, their locus, usually cracks in the walls, furniture, etc., can be sprayed or powdered. Since cockroaches are extremely vigorous and it is almost impossible to drive them away completely, it is recommended that when using the present active ingredients, insecticides having activity against cockroaches are used additionally.

For application on humans, a pleasant-smelling essence, e.g. a perfume, can be added to make application more attractive.

The following examples of preparation and usage of the active ingredients according to the invention serve to illustrate the invention without restricting it.

In particular, preferred formulations are made up as follows:

FORMULATION EXAMPLE 1

A vermin-deterring composition in the form of a lotion for application to the skin is prepared by mixing 30 parts of one of the active ingredients according to the invention from Table 1, 1.5 parts of perfume and 68.5 parts of isopropanol, whereby the latter may be replaced by ethanol.

FORMULATION EXAMPLE 2

A vermin-deterring composition in the form of an aerosol for spraying onto the pelt of a pet is prepared by formulating 50% active ingredient solution, consisting of 30 parts of one of the active ingredients according to the invention from Table 1, 1.5 parts of perfume and 68.5 parts of isopropanol, with 50% Frigen 11/12 (a halogenated hydrocarbon) as propellant gas in an aerosol can.

FORMULATION EXAMPLE 3

A vermin-deterring composition in the form of an aerosol for spraying onto the skin is prepared by formulating 40% active ingredient solution, consisting of 20 parts of one of the active ingredients according to the invention, 1 part of perfume, 79 parts of isopropanol, with 60% propane/butane (in a ratio of 15:85) as propellant gas in an aerosol can.

By way of example, the following Tables reproduce a few of the compounds included under formula (I) which can be used according to the invention, but do not claim to be a total list. The substances shown in italics are new and are part of the present invention. The remaining substances, including their preparation processes, are known from literature. The subsequent preparation example merely serves to exemplify and relates to one particularly preferred substance. Most of these known substances are used in human medicine for various illnesses, for example as bronchodilators, antiallergic agents, analgesics, diuretics, antidepressants, blood-thinning agents, etc. Some are attributed as having plant growth regulating activity; others are used as chemical catalysts or intermediates for pharmaceuticals.

To cite just one example, the preparation of representatives included in the scope of formula (I), wherein R, $R_2$, $R_3$ and $R_b$ are hydrogen, $R_1$ is hydrogen or alkyl and $R_a$ is a hydroxylated phenyl, is described in DE-3 024 436, the representatives disclosed therein being characterised as bronchodilators, antihypertensive agents and antidepressants.

PREPARATION EXAMPLE

Preparation of 2-[(1-[3-chlorophenyl])(1-hydroxy)methyl]-5,5-dimethylpyrrolidine 35.4 ml (0.24 mols) of diisopropylamine are dissolved in 350 ml of tetrahydrofuran and cooled to −75° C. under nitrogen with a bath of dry ice and acetone. At this temperature, 180 ml (0.29 mols) of an approximately 1.6 molar solution of butyl lithium in hexane are added dropwise. By removing the cooling bath, the temperature is allowed to rise to −10° C. The solution of lithium-diisopropylamine thus obtained is again cooled to −78° C. This solution is mixed over the course of 20 minutes with 32 g (0.25 mols) of 1-nitroso-2,2-dimethylpyrrolidine and stirred for a further 10 minutes. Then, 35.2 g (0.25 mols) of 3-chlorobenzaldehyde are added dropwise over the course of 15 minutes, and the mixture is stirred for a further 3 hours at −75° C. To the resulting orange-coloured solution is then added dropwise, over the course of 20 minutes, a solution of 40 ml (0.7 mols) of glacial acetic acid in 80 ml of tetrahydrofuran. The reaction mixture which is now light yellow is warmed to room temperature by removing the cooling bath, and is then poured onto a mixture of 1 liter each of saturated sodium chloride solution and methyl chloride. After shaking out, the aqueous phase is separated and washed twice, each time with 200 ml of methylene chloride. The combined organic phases are washed with 200 ml of water, dried over sodium sulphate and the solvent residues are removed in a vacuum. The crystalline residue is dissolved whilst hot in a mixture of 180 ml of toluene and 270 ml of hexane. Upon cooling, the title substance is obtained in the form of white crystals having a m.p. of 143–144° C.

The new representatives within the scope of formula (I), shown in italics in Table 1, may be prepared analogously to the known substances. In column "R", the representatives having an acid in round parenthesis are the corresponding acid addition salts.

In the following Table, Ac is acetyl, AcO is acetyloxy, Me is methyl, MeO is methoxy, Et is ethyl, EtO is ethoxy, P is propyl, PO is propoxy, nP is n-propyl, iP is iso-propyl, B is butyl, nB is n-butyl, iB is iso-butyl, sB is sec.-butyl, tB is tert.-butyl, Ph is phenyl; Bz is benzyl, cPro is cyclopropyl, cBu is cyclobutyl, cPen is cyclopentyl, cHex is cyclohexyl, cHep is cycloheptyl, cOc is cyclooctyl, and me is methylene.

TABLE 1

Compounds of formula (I)

| No. | $R_1$ | $R_2$ | $R_3$ | $R_a$ | $R_b$ | R |
|---|---|---|---|---|---|---|
| 1.01 | H | H | H | Me | H | H |
| 1.02 | 3,5-diOAc-Ph | H | H | Me | H | H |
| 1.03 | H | H | H | Et | H | H |
| 1.04 | Ph-CO— | H | H | Et | H | H |
| 1.05 | H | H | H | nP | H | H |
| 1.06 | H | H | H | iP | H | H |

TABLE 1-continued

Compounds of formula (I)

| No. | $R_1$ | $R_2$ | $R_3$ | $R_a$ | $R_b$ | R |
|---|---|---|---|---|---|---|
| 1.07 | H | H | H | nB | H | H |
| 1.08 | H | H | H | sB | H | H |
| 1.09 | H | H | H | iB | H | H |
| 1.10 | H | H | H | tB | H | H |
| 1.11 | H | H | H | -(me)$_4$-Me | H | H |
| 1.12 | H | H | H | -(me)$_5$-Me | H | H |
| 1.13 | H | 5-tB | H | -(me)$_5$-Me | H | H |
| 1.14 | H | 5-nB | H | -(me)$_5$-Me | H | H |
| 1.15 | H | H | H | -(me)$_6$-Me | H | H |
| 1.16 | H | 5-nP | H | -(me)$_6$-Me | H | H |
| 1.17 | H | H | H | -(me)$_7$-Me | H | H |
| 1.18 | H | H | H | -(me)$_8$-Me | H | H |
| 1.19 | H | H | H | -(me)$_9$-Me | H | H |
| 1.20 | H | H | H | -(me)$_{10}$-Me | H | H |
| 1.21 | H | H | H | -(me)$_{11}$-Me | H | H |
| 1.22 | H | H | H | -(me)$_{12}$-Me | H | H |
| 1.23 | H | H | H | -(me)$_{13}$-Me | H | H |
| 1.24 | H | H | H | -(me)$_{14}$-Me | H | H |
| 1.25 | H | H | H | -(me)$_{15}$-Me | H | H |
| 1.26 | H | H | H | -(me)$_{16}$-Me | H | H |
| 1.27 | H | H | H | -(me)$_{17}$-Me | H | H |
| 1.28 | H | H | H | -(me)$_{18}$-Me | H | H |
| 1.29 | H | H | H | -(me)$_{19}$-Me | H | H |
| 1.30 | H | H | H | -(me)$_{20}$-Me | H | H |
| 1.31 | H | H | H | Ph | H | H |
| 1.32 | H | H | H | Ph | H | H (HCl) |
| 1.33 | H | 5-Me | 5-Me | Ph | H | H |
| 1.34 | H | 5-Me | 5-Me | Ph | H | H (HCl) |
| 1.35 | H | H | H | 3-Cl-Ph | H | H |
| 1.36 | H | H | H | 3-CF$_3$-Ph | H | H (HCl) |
| 1.37 | H | 5-Me | 5-Me | 3-Cl-Ph | H | H |
| 1.38 | H | 5-Me | 5-Me | 3-Cl-Ph | H | H (HCl) |
| 1.39 | H | 5-Me | 5-Me | 3-CF$_3$-Ph | H | H |
| 1.40 | H | 5,5-diMe | H | 3-CF$_3$-Ph | H | H (HCl) |
| 1.41 | H | 5-Me | 5-Me | 3-Me-Ph | H | H |
| 1.42 | H | 5-Me | 5-Me | 3-Me-Ph | H | H (HCl) |
| 1.43 | H | 5-Me | 5-Me | 3-CN-Ph | H | H |
| 1.44 | H | 5-Me | 5-Me | 3-CN-Ph | H | H (HCl) |
| 1.45 | H | H | H | 4-Cl-Ph | H | H |
| 1.46 | H | H | H | 4-Cl-Ph | H | H (HCl) |
| 1.47 | H | 2-Me | 2-Me | 4-Cl-Ph | H | H |
| 1.48 | H | 5-Me | 5-Me | 4-Cl-Ph | H | H |
| 1.49 | H | 5-Me | 5-Me | 4-Me-Ph | H | H |
| 1.50 | H | H | H | 4-Br-Ph | H | H |
| 1.51 | H | H | H | 4-F-Ph | H | H |
| 1.52 | H | H | H | 4-MeO-Ph | H | H |
| 1.53 | H | H | H | 4-tB-Ph | H | H |
| 1.54 | H | H | H | 4-cHex-Ph | H | H |
| 1.55 | H | 2-Me | 2-Me | 2,4-diMe-Ph | H | H |
| 1.56 | H | H | H | 3,4-diOH-Ph | H | H |
| 1.57 | H | H | H | 3,4-diOH-Ph | H | H (HCl) |
| 1.58 | H | 5-Me | 5-Me | 3,4-diCl-Ph | H | H |
| 1.59 | H | 5-Me | 5-Me | 3,4-diCl-Ph | H | H (HCl) |
| 1.60 | H | 5-Me | 5-Me | 2,6-diCl-Ph | H | H |
| 1.61 | H | 5-Me | 5-Me | 2,6-diCl-Ph | H | H (HCl) |
| 1.62 | H | 5-Me | 5-Me | 2,4-diCi-Ph | H | H |
| 1.63 | H | 5-Me | 5-Me | 2,4-diCl-Ph | H | H (HCl) |
| 1.64 | H | H | H | 2,3,6-triMeO-Ph | H | H |
| 1.65 | H | H | H | 2,3,6-triMeO-Ph | Me | H |
| 1.66 | H | H | H | 4-CF$_3$-Ph | 4-CF$_3$-Ph | H |
| 1.67 | H | H | H | 4-CF$_3$-Ph | 4-CF$_3$-Ph | H (HCl) |
| 1.68 | H | H | H | 3-Cl-Ph | 3-Cl-Ph | H |
| 1.69 | H | H | H | 4-MeO-Ph | 4-MeO-Ph | H |
| 1.70 | H | H | H | 4-Me-Ph | 4-Me-Ph | H |
| 1.71 | H | H | H | 4-F-Ph | 4-F-Ph | H |
| 1.72 | H | H | H | 4-tB-Ph | 4-tB-Ph | H |
| 1.73 | H | H | H | 4-vinyl-Ph | 4-vinyl-Ph | H |
| 1.74 | H | H | H | 3,5-di-Cl-Ph | 3,5-di-Cl-Ph | H |
| 1.75 | H | H | H | 3,5-di-CF$_3$—Ph | 3,5-di-CF$_3$—Ph | H |

TABLE 1-continued

Compounds of formula (I)

| No. | $R_1$ | $R_2$ | $R_3$ | $R_a$ | $R_b$ | R |
|---|---|---|---|---|---|---|
| 1.76 | H | H | H | 3-Me-4-F—Ph | 3-Me-4-F—Ph | H |
| 1.77 | H | H | H | Ph | Me | H |
| 1.78 | H | H | H | Ph | Ph | H |
| 1.79 | H | H | H | Ph | Ph | H (HCl) |
| 1.80 | Ph-CO— | H | H | Ph | Ph | H |
| 1.81 | 2-CHO-Ph-CO— | H | H | Ph | Ph | H |
| 1.82 | 2-AcO-Ph-CO— | H | H | Ph | Ph | H |
| 1.83 | Me | H | H | Ph | Ph | H |
| 1.84 | Me | H | H | Ph | H | H |

BIOLOGICAL EXAMPLES

Arena Test Method for Testing Vermin-repellent Substances

This method is carried out in titre plates having 6 wells with a cross-section of 5 cm each, using a computer-supported video system. Each well of the titre plate is lined with a circular filter paper or another suitable carrier material. The substance of formula I to be tested is dissolved in methanol, acetonitrile or another suitable solvent, with ultrasound treatment and heating being employed for poorly-soluble substances. In an amount of 1 to 100 $\mu g/cm^2$, the dissolved test substance is placed in the centre of the filter paper on a quadrant or circular area of ca. 2.4 $cm^2$ radius. 4 of the 6 wells are filled with different test substances or with the same test substance in different dilutions (e.g. 1, 3.2, 5, 10 and 20 $\mu g/cm^2$). The 5th well is treated with DEET (N,N-diethyl-m-toluamide) as standard substance. The 6th well is filled with the pure solvent and serves as a control. 60 to 100 larvae or 25 to 50 nymphs or 10 to 25 adults of the parasite to be tested, e.g. ticks, are added to each filter paper, and the system is covered with a pane of glass and positioned under a video camera. At intervals of 5 seconds, the video camera takes individual pictures of all 6 wells. For a qualitative evaluation, these images are observed in a time-lapse as a continuous film, optically following the movements of the parasites on the filter paper and comparing them with the movements in the control well no. 6 or with the standard in the 5th well. A qualitative observation is thus made as to whether the test parasites move evenly over the whole surface of the filter paper and ignore the test substance, or whether and over what period they avoid the treated zone, and what influence the dilution of the test substance has on the behaviour of the test parasites. In this way, neutral and repellent substances are determined. At the same time, the duration of activity of the test substance is determined and compared with that of the standard. By plotting all the images for each individual well over one another, different areas of density are obtained. This represents the frequency at which the parasites visit certain places. This frequency is evaluated statistically and thus quantitatively by the Willcoxon method in a comparison with the control and with the standard. Compounds of Table 1, for example nos. 1.11 to 1.31, 1.45, 1.47 and 1.55, display excellent activity.

Arena Test in vitro Against *Amblyomma hebraeum* or *variegatum* (Nymphs)

The test is carried out as described above, with ca. 25 to 50 nymphs being added per well. 10 mg of dissolved test substance is applied to an area of 2.4 $cm^2$ radius. An evaluation of the video images shows that the compounds of formula I display marked deterrent action against Amblyomma nymphs, which lasts considerably longer than that of DEET. Particularly marked long-term activity is shown for example by compounds nos. 1.31, 1.45, 1.47 and 1.55, even up to a dilution of 3.2 $\mu g/cm^2$.

Arena Test in vitro Against *Boophilus microplus Biarra* (Larvae)

The test is carried out as described above, with ca. 60 to 100 larvae being added per well. 10 mg of dissolved test substance is applied to an area of 2.4 $cm^2$ radius. An evaluation of the video images shows that the compounds of formula I display marked repellent action against Bophilus larvae, which lasts considerably longer than that of DEET. Particularly marked long-term activity is shown for example by compounds nos. 1.31, 1.45, 1.47 and 1.55, even up to a dilution of 3.2 $\mu g/cm^2$.

Arena Test in vitro Against *Rhipicephalus sanguineus* (Nymphs)

A test is carried out analogously to example B using ca. 40 to 50 nymphs. An evaluation of the video images shows that the compounds according to the invention display good repellent action. In particular, the compounds are notable for their almost complete repellent action, which lasts considerably longer than that of DEET. Particularly marked long-term activity is shown for example by compounds nos. 1.31, 1.45, 1.47 and 1.55, even up to a dilution of 3.2 $\mu g/cm^2$.

In analogous test set-ups, the same test substances are tested for their attractant activity to various species of fly, such as *Musca domestica*. It is shown that the substances mentioned above display strong repellent action even with these tested models.

What is claimed is:

1. A process for protecting warm-blooded animals from pests comprising the application of an effective pesticidal amount of a compound of formula (I)

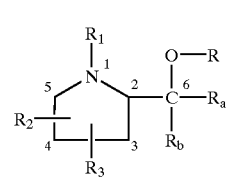

(I)

or one of its acid addition salts, wherein

R is hydrogen, $C_1$–$C_{20}$-alkyl or —C(O)—$R_8$; whereby $R_8$ is $C_1$–$C_{20}$-alkyl, $C_1$–$C_{20}$-alkoxy, unsubstituted phenyl or phenyl which is substituted once or many times by $C_1$–$C_3$-alkyl, $C_1$–$C_3$-haloalkyl, $C_1$–$C_3$-haloalkoxy, halogen, cyano, hydroxyl, alkoxy, amino or nitro;

$R_1$ is hydrogen, $C_1$–$C_{20}$-alkyl, —C(O)—$R_3$, —C(S)—$R_4$, C(O)—O—$R_5$, —C(O)—NH—$R_6$ or —C(S)—NH—$R_7$; whereby $R_3$, $R_4$, $R_5$, $R_6$ and $R_7$, independently of one another, signify $C_1$–$C_{10}$-alkyl, acetoxy, $C_1$–$C_{10}$-haloalkyl, $C_1$–$C_{10}$-alkoxy or $C_1$–$C_{10}$-haloalkoxy, or independently of one another, denote unsubstituted phenyl or phenyl which is substituted once or many times by $C_1$–$C_3$-alkyl, $C_1$–$C_3$-haloalkyl, $C_1$–$C_3$-haloalkoxy, halogen, cyano, hydroxyl, $C_1$–$C_3$-alkoxy, amino, CHO or nitro;

$R_2$ and $R_3$, independently of one another, are hydrogen, $C_1$–$C_3$-alkyl, $C_1$–$C_3$-haloalkyl, $C_1$–$C_3$-haloalkoxy, halogen, cyano, hydroxyl, amino, aryl or nitro;

$R_a$ denotes hydrogen, unsubstituted $C_1$–$C_{20}$-alkyl or $C_1$–$C_{20}$-alkyl which is substituted once or many times by halogen, cyano, hydroxyl, alkoxy, nitro, phenyl, biphenyl, benzyloxy or phenoxyphenyl, whereby each phenyl, biphenyl, benzyloxy or phenoxyphenyl in turn is unsubstituted or substituted once or many times by $C_1$–$C_3$-alkyl, $C_1$–$C_3$-haloalkyl, $C_1$–$C_3$-haloalkoxy, $C_1$–$C_3$-alkoxy, halogen, cyano, hydroxyl, amino or nitro; or it denotes $C_3$–$C_8$-cycloalkyl, phenyl, biphenyl, phenoxyphenyl or heterocyclyl, whereby each of these cyclic radicals is unsubstituted or substituted once or many times by $C_1$–$C_3$-alkyl, $C_2$–$C_6$-alkenyl, $C_1$–$C_3$-haloalkyl, $C_1$–$C_3$-haloalkoxy, $C_1$–$C_3$-alkoxy, halogen, cyano, hydroxyl, amino, ($C_1$–$C_3$-alkyl)$_2$N, acetyl or nitro; or it denotes $C_{-C6}$-alkylene-aryl, whereby the aryl radical is unsubstituted or substituted once or many times by $C_1$–$C_3$-alkyl, $C_1$–$C_3$-haloalkyl, $C_1$–$C_3$-haloalkoxy, halogen, cyano, hydroxyl or nitro; or it denotes $C_1$–$C_{20}$-alkyl which, depending on the number of carbon atoms, is interrupted by oxygen at one or several positions; and $R_b$ signifies hydrogen, $C_1$–$C_{20}$-alkyl, heterocyclyl or aryl, whereby each of the cyclic radicals is unsubstituted or substituted once or many times by $C_1$–$C_3$-alkyl, $C_1$–$C_3$-haloalkyl, $C_1$–$C_3$-haloalkoxy, $C_2$–$C_6$-alkenyl, halogen, cyano, hydroxyl, $C_1$–$C_3$-alkoxy, amino,($C_1$–$C_3$-alkyl)$_2$N, or nitro; together with a spreading additive, to the skin, the pelt or the plumage of the warm-blooded animal.

2. The process according to claim 1, comprising the application of the compound of formula (I) or one of its acid addition salts, wherein R is hydrogen or $C_1$–$C_6$alkyl;

$R_1$ is hydrogen, $C_1$–$C_6$-alkyl, —C(O)—$R_3$ or —C(S)—$R_4$; whereby $R_3$ and $R_4$ independently of one another, are $C_1$–$C_3$-alkyl, acetoxy, $C_1$–$C_3$-haloalkyl, or independently of one another, are unsubstituted phenyl or phenyl which is substituted once or more by $C_1$–$C_3$-alkyl, $C_1$–$C_3$-haloalkyl or halogen;

$R_2$ and $R_3$ independently of one another, are hydrogen or $C_1$–$C_3$-alkyl;

$R_a$ is hydrogen, $C_5$–$C_{20}$-alkyl, $C_3$–$C_8$-cycloalkyl or phenyl, whereby each of the cyclic radicals is unsubstituted or is substituted once or many times by $C_1$–$C_3$-alkyl, $C_1$–$C_3$-haloalkyl, $C_1$–$C_3$-alkoxy, halogen, amino, ($C_1$–$C_3$-alkyl)$_2$N, or acetyl; and $R_b$ is hydrogen, unsubstituted phenyl or phenyl which is substituted once or many times by $C_1$–$C_3$-alkyl, $C_1$–$C_3$-haloalkyl, $C_1$–$C_3$-alkoxy, halogen, amino or ($C_1$–$C_3$-alkyl)$_2$N; including the acid addition salts thereof.

3. The process according to claim 1, comprising the application of the compound of formula (I) or one of its acid addition salts, wherein R is hydrogen.

4. The process according to claim 1 comprising the application of the compound of formula (I) or one of its acid addition salts, wherein $R_1$ is —C(O)—$R_3$, $R_3$ represents unsubstituted phenyl or phenyl which is substituted once or more by $C_1$–$C_3$-alkyl.

5. The process according to claim 1 comprising the application of the compound of formula (I) or one of its acid addition salts, wherein $R_2$ and $R_3$, independently of each other, are hydrogen or methyl.

6. The process according to claim 1 comprising the application of the compound of formula (I) or one of its acid addition salts, wherein $R_a$ is $C_5$–$C_{20}$-alkyl, unsubstituted phenyl or phenyl which is substituted once or more by $C_1$–$C_3$-alkyl, methoxy or chlorine.

7. The process according to claim 1 comprising the application of the compound of formula (I) or one of its acid addition salts, wherein $R_a$ is a straight-chained $C_7$–$C_{20}$-alkyl.

8. The process according to claim 1, comprising the application of the compound of formula (I) or one of their acid addition salts selected from the group consisting of:

2-[n-(1-hydroxyhexyl)]pyrrolidine, 2-[n-(1-hydroxyheptyl)]pyrrolidine,

2-[n-(1-hydroxyheptyl)]-5-(tert.-butyl)pyrrolidine, 2-[n-(1-hydroxyheptyl)]-5-(n-butyl)pyrrolidine 2-[n-(1-hydroxyoctyl)]pyrrolidine, [n-(1-hydroxyoctyl)]-5-(n-propyl)-pyrrolidine, 2-[n-(1-hydroxynonyl)]pyrrolidine, 2-[n-(1-hydroxydecyl)]pyrrolidine, 2-[n-(1-hydroxyundecyl)]pyrrolidine, 2-[n-(1-hydroxydodecyl)]pyrrolidine, 2-[n-(1-hydroxytridecyl)]-pyrrolidine, 2-[n-(1-hydroxytetradecyl)]pyrrolidine, 2-[n-(1-hydroxypentadecyl)]pyrrolidine, 2-[n-(1-hydroxyhexadecyl)]pyrrolidine, 2-[n-(1-hydroxyheptadecyl)]pyrrolidine, 2-[n-(1-hydroxyoctadecyl)]pyrrolidine, 2-[n-(1-hydroxynonadecyl)]pyrrolidine, 2-[n-(1-hydroxyeicosyl)]pyrrolidine, 2-[n-(1-hydroxyeneicosyl)]pyrrolidine, 2-[(1-phenyl)(1-hydroxy)-methyl]pyrrolidine, 2-[(1-[4-chorophenyl])(1-hydroxy)methyl]pyrrolidine 2-[(1-[2,4-dimethylphenyl])(1-hydroxy)methyl]-5,5-dimethyl-pyrrolidine and 2-[(1-[3chlorophenyl])(1-hydroxy)methyl]-5,5-dimethyl-pyrrolidine.

9. The process according to claim 1 wherein the compound of formula (I) is applied in the form of a pour-on or spot-on formulation.

10. A process for controlling pests comprising the application of an effective amount of a compound of formula (I) according to claim 1 to the pest or its habitat.

11. A topical repellent composition for topically controlling pests, comprising a compound of formula (I)

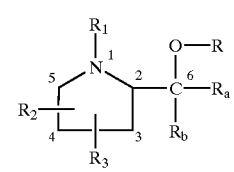

or one of its acid addition salts, and a suitable carrier, wherein

R is hydrogen, $C_1$–$C_{20}$-alkyl or —C(O)—$R_8$, wherein $R_8$ is $C_1$–$C_{20}$-alkyl, $C_1$–$C_{20}$-alkoxy, unsubstituted phenyl or phenyl which is substituted by $C_1$–$C_3$-alkyl, $C_1$–$C_3$- haloalkyl, $C_1$–$C_3$-haloalkoxy, halogen, cyano, hydroxyl, alkoxy, amino or nitro;

$R_1$ is hydrogen, $C_1$–$C_{20}$-alkyl, —C(O)—$R_3$, —C(S)—$R_4$, C(O)—O—$R_5$, —C(O)—NH—$R_6$ or —C(S)—NH—$R_7$, wherein $R_3$, $R_4$, $R_5$, $R_6$ and $R_7$, independently of one another, signify $C_1$–$C_{10}$-alkyl, acetoxy, $C_1$–$C_{10}$-haloalkyl, $C_1$–$C_{10}$-alkoxy or $C_1$–$C_{10}$-haloalkoxy, or independently of one another, denote unsubstituted phenyl or phenyl which is substituted by $C_1$–$C_3$-alkyl, $C_1$–$C_3$-haloalkyl, $C_1$–$C_3$-haloalkoxy, halogen, cyano, hydroxyl, $C_1$–$C_3$-alkoxy, amino, CHO or nitro;

$R_2$ and $R_3$, independently of one another, are hydrogen, $C_1$–$C_3$-alkyl, $C_1$–$C_3$-haloalkyl, $C_1$–$C_3$-haloalkoxy halogen, cyano, hydroxyl, amino, aryl or nitro;

$R_a$ denotes hydrogen, unsubstituted $C_1$–$C_{20}$-alkyl or $C_1$–$C_{20}$-alkyl which is substituted by halogen, cyano, hydroxyl, alkoxy, nitro, phenyl, biphenyl, benzyloxy or phenoxyphenyl, wherein each phenyl, biphenyl, benzyloxy or phenoxyphenyl in turn is unsubstituted or substituted by $C_1$–$C_3$-alkyl, $C_1$–$C_3$-haloalkyl, $C_1$–$C_3$-haloalkoxy, $C_1$–$C_3$-alkoxy, halogen, cyano, hydroxyl, amino or nitro; or it denotes $C_3$–$C_8$-cycloalkyl, phenyl, biphenyl, phenoxyphenyl or heterocyclyl, wherein each of these cyclic radicals is unsubstituted or substituted by $C_1$–$C_3$-alkyl, $C_2$–$C_6$-alkenyl, $C_1$–$C_3$-haloalkyl, $C_1$–$C_3$-haloalkoxy, $C_1$–$C_3$-alkoxy, halogen, cyano, hydroxyl, amino, $(C_1$–$C_3$-alkyl$)_2$N, acetyl or nitro; or it denotes $C_1$–$C_6$-alkylene-aryl, wherein the aryl radical is unsubstituted or substituted by $C_1$–$C_3$-alkyl, $C_1$–$C_3$-haloalkyl, $C_1$–$C_3$-haloalkoxy, halogen, cyano, hydroxyl or nitro; or it denotes $C_1$–$C_{20}$-alkyl which, depending on the number of carbon atoms, is interrupted by oxygen at one or several positions; and $R_b$ signifies hydrogen, $C_1$–$C_{20}$-alkyl, heterocyclyl or aryl, wherein each of the cyclic radicals is unsubstituted or substituted by $C_1$–$C_3$-alkyl, $C_1$–$C_3$-haloalkyl, $C_1$–$C_3$-haloalkoxy, $C_2$–$C_6$-alkenyl, halogen, cyano, hydroxyl, $C_1$–$C_3$-alkoxy, amino, $(C_1$–$C_3$-alkyl$)_2$N, or nitro.

12. A process for the preparation of a topical repellent composition for controlling pests, comprising mixing a compound of formula (I) according to claim 11 with a suitable carrier, wherein said composition is topically appliable.

13. The topical repellent composition according to claim 11, wherein formula (I) is selected from the group consisting of:

2-[n-(1-hydroxyhexyl)]pyrrolidine, 2-[n-(1-hydroxyheptyl)]pyrrolidine, 2-[n-(1-hydroxyoctyl)]pyrrolidine, 2-[n-(1-hydroxynonyl)]pyrrolidine, 2-[n-(1-hydroxydecyl)]pyrrolidine, 2-[n-(1-hydroxyundecyl)]pyrrolidine, 2-[n-(1-hydroxydodecyl)]pyrrolidine, 2-[n-(1-hydroxytridecyl)]-pyrrolidine, 2-[n-(1-hydroxytetradecyl)]pyrrolidine, 2-[n-(1-hydroxypentadecyl)]pyrrolidine, 2-[n-(1-hydroxyhexadecyl)]pyrrolidine, 2-[n-(1-hydroxyheptadecyl)]pyrrolidine, 2-[n-(1-hydroxyoctadecyl)]pyrrolidine, 2-[n-(1-hydroxynonadecyl)]pyrrolidine, 2-[n-(1-hydroxyeicosyl)]pyrrolidine and 2-[n-(1-hydroxyeneicosyl)]pyrrolidine.

14. The process according to claim 4 wherein $R_3$ represents phenyl substituted once or more by alkyl substituents selected from the group consisting of methyl, ethyl or isopropyl.

15. The process according to claim 1 wherein the pests are selected from the group consisting of insects and acarina.

* * * * *

UNITED STATES PATENT AND TRADEMARK OFFICE
CERTIFICATE OF CORRECTION

PATENT NO.     : 6,458,826 B2
DATED          : October 1, 2002
INVENTOR(S)    : Froelich et al.

It is certified that error appears in the above-identified patent and that said Letters Patent is hereby corrected as shown below:

Title page,
Item [73] should read:
-- [73]  Assignee:  Novartis Animal Health US, Inc., --

Column 13,
Line 28, should read:
-- nitro; or it denotes $C_1$-$C_6$-alkylene-aryl, whereby the --

Column 14,
Line 44, should read:
-- dimethyl-pyrrolidine and 2-[(3-chlorophenyl])(1- --

Signed and Sealed this

First Day of July, 2003

JAMES E. ROGAN
*Director of the United States Patent and Trademark Office*